United States Patent
Bommer et al.

(10) Patent No.: US 9,903,880 B2
(45) Date of Patent: Feb. 27, 2018

(54) INSTRUMENT AND METHOD FOR AUTOMATICALLY HEAT-SEALING A MICROPLATE

(75) Inventors: Daniel Bommer, Winterthur (CH); Thomas Schlaubitz, Meggen (CH); Pius Studer, Lucerne (CH)

(73) Assignee: Roche Molecular Systems, Inc., Pleasanton, CA (US)

( * ) Notice: Subject to any disclaimer, the term of this patent is extended or adjusted under 35 U.S.C. 154(b) by 402 days.

(21) Appl. No.: 13/286,853

(22) Filed: Nov. 1, 2011

(65) Prior Publication Data
US 2012/0288923 A1 Nov. 15, 2012

(30) Foreign Application Priority Data
Nov. 2, 2010 (EP) .................................. 10189640

(51) Int. Cl.
- *B65B 7/28* (2006.01)
- *G01N 35/02* (2006.01)
- *B29C 65/00* (2006.01)
- *B01L 3/00* (2006.01)
- *G01N 35/04* (2006.01)

(52) U.S. Cl.
CPC ........ *G01N 35/028* (2013.01); *B01L 3/50853* (2013.01); *B29C 66/53461* (2013.01); *B65B 7/2878* (2013.01); *G01N 35/026* (2013.01); *G01N 2035/0405* (2013.01)

(58) Field of Classification Search
CPC .... B29C 66/53461; B65B 7/28; B65B 7/2878
See application file for complete search history.

(56) References Cited

U.S. PATENT DOCUMENTS

| | | | |
|---|---|---|---|
| 4,969,965 A * | 11/1990 | Matty et al. | 156/69 |
| 5,582,665 A | 12/1996 | Eigen et al. | |
| 6,413,334 B1 * | 7/2002 | Rittner | B29C 65/18 156/228 |
| 6,451,261 B1 | 9/2002 | Bodner et al. | |
| 6,719,678 B1 * | 4/2004 | Stern | 493/212 |
| 2008/0141623 A1 * | 6/2008 | Stowell | 53/287 |

FOREIGN PATENT DOCUMENTS

| | | |
|---|---|---|
| EP | 1974818 A1 | 10/2008 |
| GB | 2461182 A | 12/2009 |

* cited by examiner

*Primary Examiner* — Jonathan M Hurst
(74) *Attorney, Agent, or Firm* — Pamela C. Ancona; M. Reza Savari

(57) ABSTRACT

A heating device for heating a thermally fixable sealing cover disposed over the microplate adjacent the wells, a cooling device for actively cooling the microplate and a controller set up to control activity of the heating and cooling devices in a manner to heat the sealing cover so as to thermally fix it to the microplate and to actively cool the microplate so as to keep a temperature of the samples below a predefined temperature when heating the sealing cover. It further relates to a method for automatically sealing a microplate in which the thermally fusible sealing cover is disposed over the microplate, the sealing cover is heated to thermally fix it to the microplate and the microplate is actively cooled in a manner that a temperature of the liquid reaction mixtures is kept below a predefined temperature when heating the sealing cover.

6 Claims, 3 Drawing Sheets

INSTRUMENT AND METHOD FOR AUTOMATICALLY HEAT-SEALING A MICROPLATE

CROSS-REFERENCES TO RELATED APPLICATIONS

The present application claims the benefit of priority under 35 U.S.C. § 119 of EP10189640.5, filed Nov. 2, 2010, the contents of which is incorporated by reference herein in its entirety.

FIELD OF THE INVENTION

The present invention is in the field of clinical analysis and medical diagnostics and more particularly relates to an instrument and method for automatically heat-sealing a microplate. It further pertains to a system for thermally processing liquid samples such as reaction mixtures.

BACKGROUND OF THE INVENTION

In these days, nucleic acids (DNA=deoxyribonucleic acid, RNA=ribonucleic acid) are subject to various analyses and assays in clinical analysis and medical diagnostics. Since the initial amount of nucleic acids normally is very low, nucleic acids have to be amplified prior to their use so as to obtain sufficient amounts which can be used as starting material.

The amplification of nucleic acids using the well-known polymerase chain reaction (PCR) has been extensively described in the patent literature, for instance, in U.S. Pat. Nos. 468,203, 4,683,195, 4,800,159 and 4,965,188. Generally, in the polymerase chain reaction, samples containing reaction mixtures of specific reagents and nucleic acids are repeatedly put through a sequence of amplification steps. Each sequence includes a step of melting the double-stranded nucleic acids to obtain denaturated single polynucleotide strands, a step of annealing short primers to the strands and a step of extending those primers to synthesize new polynucleotide strands along the denaturated strands to make new copies of double-stranded nucleic acids. Due to the fact that reaction conditions strongly vary with temperatures, the samples are put through a series of temperature excursions in which predetermined temperatures are kept constant for specific time intervals ("thermo-cycling"). The temperature of the samples typically is raised to around 90° C. for melting the nucleic acids and lowered to a temperature in the range of from 40° C. to 70° C. for annealing and primer extension along the polynucleotide strands. It is known to detect the reaction products even during the progress of the polymerase chain reaction ("real-time PCR") to thereby obtain more information about the amplification process and to improve the reliability of the detection results.

In daily routine, the PCR is performed in commercially available instruments enabling a large number of reaction mixtures to be cycled simultaneously. Usually, integrally molded plastic disposables provided with plural open-top wells sized to receive the reaction mixtures are used for nucleic acid amplification. Such disposables are commonly known as "microplates".

It has been found advantageous to provide the open-top wells with a sealing cover for air-tightly sealing individual wells containing the reaction mixtures. One reason is the necessity to avoid evaporation of liquids so as to ensure the integrity of the reaction mixtures. Another reason is to prevent spilling of the contents of the wells during transport of the microplate from one location to another. A yet another reason is to prevent cross contamination of individual reaction mixtures contained in the wells so as to provide a generally sterile and controlled environment under which the amplification steps can be carried out.

It is convenient to use transparent sealing covers such as thin plastic foils applied to the top surface of the microplate which allow for an optical detection of the reaction products even during progress of the reactions. In practical use, for instance, an adhesive plastic foil provided with an adhesive backing is positioned over the microplate so that the adhesive backing faces the upper surface of the microplate. The plastic foil then is pressed on the upper surface, e.g., by means of a pressure roll rolling back and forth to thereby obtain uniform adhesion of the sealing foil to the microplate. Adhesive foils, however, often cause problems with respect to an air-tight sealing of individual wells. Accordingly, undesired evaporation of fluids impairing the reproducibility of test results especially in the case of small sample volumes and cross contamination between various reaction mixtures may occur. Otherwise, the adhesive material may probably influence the outcome of the nucleic acid amplification steps thus downgrading the reliability of the test results.

Better results can normally be obtained using thermally fusible foils. In practical use, the foil is positioned over the microplate and heated, e.g., by means of a heated sealing stamp which can be brought in and out of contact with the foil. While heated, the sealing foil is pressed onto the microplate to ensure a close adhesive fit with full contact to the microplate.

In light of the foregoing, it is an object of the invention to provide an improved instrument and method for automatically heat-sealing microplates. It is a further object of the invention to provide an improved system for processing, especially thermally processing, and/or analyzing liquid samples. These and further objects are met by an instrument and method for thermally heat-sealing microplates as well as a system for thermally processing liquid samples according to the independent claims. Preferred embodiments of the invention are given by the features of the dependent claims.

SUMMARY OF THE INVENTION

According to a first aspect of the invention, a new instrument for the automated heat-sealing of a microplate using a thermally fixable sealing cover is proposed. In some embodiments, the microplate has an upper surface and an opposing lower surface wherein a plurality of open-top retention regions or wells for receiving liquid samples such as reaction mixtures is formed in the upper surface.

In some embodiments, the instrument of the invention comprises a heating device for heating the thermally fixable sealing cover disposed over the microplate adjacent the wells. In some embodiments, the thermally fixable sealing cover is a thermally fusible sealing cover. In some alternative embodiments, the sealing cover is provided with an adhesive material which can be thermally activated. Such adhesive materials are well-known to those of skill in the art and, e.g., are described in U.S. Pat. No. 7,037,580. In some embodiments, the heating cover is disposed on the upper plate surface of the microplate. Heated by the heating device, in some embodiments, the sealing cover can at least locally be heated, e.g., fused so as to induce adherence to the microplate, e.g., going along with solidification of the sealing cover in order to air-tightly seal each of the wells. For heating the sealing cover, the heating device can be brought in and out of thermal communication with the sealing cover. In some embodiments the heating device can also be brought in and out of direct (physical) contact with the sealing cover, especially, in order to press the sealing cover on the microplate. In some embodiments, the sealing cover is configured as transparent sealing cover enabling optical detection of reaction products contained in the wells. In some embodiments, the heating device is adapted to be operated to heat or alternatively actively cool the sealing cover. In the latter case, the heating device can, e.g., include one or more thermoelectric devices (Peltier devices) which can generate or absorb heat according to the direction of the current applied. Accordingly, solidification of the sealing cover can advantageously be accelerated.

In some embodiments, the instrument of the invention comprises a cooling device for actively cooling the microplate. In some embodiments, the cooling device comprises a casing forming an internal space which can be actively cooled. The internal space preferably accommodates the heating device for thermally fixing the sealing cover to the microplate in an actively cooled environment. It is preferred to accommodate a heating device having a low thermal capacity in the internal space. In some embodiments, the casing is a closed casing. As used herein, the term "closed casing" relates to a casing which contrary to the strict sense of the term can be provided with one or more openings or ports, e.g., to transfer microplates into and out of the internal space. In some embodiments, the casing is provided with one or more ports which are configured to be brought in a temporarily opened or closed state. Generally, the closed casing which can be provided with one or more ports serves to restrict or reduce the input of heat and liquid fluids to the internal space so as to provide a controlled environment in order to prevent contamination of liquid samples contained therein. In some embodiments, the closed casing is provided with at least one microplate port which can be closed or opened for transporting the microplate in or out of the internal space. The internal space can be actively cooled by a cooling means in thermal communication with the internal space. In some embodiments the cooling means is a cooling coil adapted for circulating cooling fluid. In some other embodiments, one or more thermoelectric devices based on the Peltier effect are used for cooling the internal space. As is known to the skilled persons, when passing electric current through a Peltier device, depending on the direction of current applied, the Peltier device functions as heat sink which absorbs heat or as heat source which releases heat to thereby cool or heat the internal space. In some embodiments, the cooling device is integrated in the heating device, that is to say, the heating and cooling device has a cooling and heating function. In this case, the heating and cooling devices, e.g., are configured as one or more thermoelectric devices for both heating and cooling the liquid samples. In some embodiments, the instrument of the invention comprises a controller set up to control activity of each of the heating and cooling devices in a manner to heat the sealing cover so as to thermally fix it to the microplate and to actively cool the microplate so as to keep the temperature of the liquid samples contained in the wells below a predefined temperature.

In some embodiments related to the PCR, the microplate is actively cooled in a manner to keep the temperature of the liquid samples contained in the wells below a predefined critical temperature lower than the temperature excursions of the nucleic acid amplification steps when heating the sealing cover. The predefined critical temperature is considered critical for starting the nucleic acid amplification. In other words, the predefined critical temperature is selectively chosen to prevent the start of any unspecific (inadvertent) nucleic acid amplification caused by heat-sealing the microplate prior to thermally cycling the reaction mixtures. In some embodiments, the predefined critical temperature is chosen to be 40° C. so that the temperature of the liquid reaction mixtures is always below 40° C. during the heat-sealing process. In some embodiments the predefined critical temperature is selected from a temperature range of from 32° C. to 40° C. In the latter case, the predefined critical temperature may, e.g., be selected from the group of temperatures consisting of 39° C., 38° C., 37° C., 36° C., 35° C., 34° C., 33° C. and 32° C. Otherwise, in some embodiments, dependent on the temperature of the reaction mixtures prior to starting the heat-sealing, it can be preferred that a temperature raise of the liquid reaction mixtures caused by heat-sealing the microplate is lower than 4° C. In some embodiments it may be preferred that the temperature raise is lower than 3° C., more preferably lower than 2° C. or even more preferably lower than 1° C. The instrument of the invention thus enables a precise temperature control of the reaction mixtures preventing any unspecific nucleic acid amplification prior to thermal cycling so as to improve the reliability and reproducibility of the nucleic acid amplification.

In some embodiments, the controller is set up to actively cool the microplate simultaneously with heating the sealing cover. In some embodiments, the controller is set up to actively cool the microplate prior to heating the sealing cover. In some embodiments, the controller is set up to actively cool the microplate prior to and simultaneously with heating the sealing cover.

In some embodiments, the instrument of the invention comprises a base and a base-mounted holder adapted for holding the microplate. In some embodiments, the holder is configured as tray slidably mounted to the base for a repetitive, bidirectional movement between an operative position for thermally fixing the sealing cover to the microplate and an inoperative position for loading or unloading the microplate to/from the holding tray. In some embodiments, the sealing arrangement includes a moving mechanism for moving the holding tray between its operative and inoperative positions. In some other embodiments, the holding tray can be manually moved between its operative and inoperative positions. In some embodiments comprising a casing forming an actively cooled internal space as above-detailed, the inoperative position is located outside the casing. Due to the microplate port which can be opened or closed, a considerable increase of the temperature of the actively cooled internal space of the casing an advantageously be prevented.

In some embodiments, the heating device comprises a supporting layer provided with at least one electrically conductive heating element adapted for generating Ohmic heat. In some embodiments, the supporting layer is made of an electrically isolating material. In some embodiments, the heating element is applied to an outer surface of the supporting layer. In some embodiments, the heating element is a meshed structure consisting of electrically conductive lines which, e.g., can be configured as conductive wires.

In some embodiments, the supporting layer is made of material having low thermal capacity such as ceramic material or plastic material like polyimide. Accordingly, the heating device can quickly be heated and cooled enabling a time- and cost-efficient sealing of the microplate. Otherwise, a major advantage is given by the fact that only little heat is lost in the instrument thus improving power efficiency in operating the instrument. Another advantage of a heating device having low thermal capacity is given by the fact that it can be located inside the casing of a cooling device forming an internal space which can be actively cooled.

In some embodiments, especially in case of using materials having low thermal capacity, the supporting layer can, e.g., have a layer thickness of less than 3 mm so as to reduce the total energy up-take of the supporting layer. It can be preferred that the supporting layer has a layer thickness of, e.g., 1.0 mm or 0.5 mm or less.

In some embodiments, the heating device is provided with a plurality of non-heated zones arranged in opposite relationship with respect to openings of the wells when the heating device is in thermal communication and eventually in physical contact with the sealing cover. Accordingly, the sealing cover can be heated exclusively in regions where adhesion to the microplate is to be reached so as to reduce the heat load of the microplate and to reduce the temperature raise of the microplate. In some embodiments, the non-heated zones are configured by gaps between the electrically conductive wires of the meshed heating element.

In some embodiments the heating device comprises one or more Peltier elements to generate the heat for sealing. When using a Peltier element the same element can also be used to cool the sealing zone in order to accelerate solidification of the sealing foil.

In some embodiments the heating device is adapted to generate the heat for sealing the sealing cover onto the microplate by inductive heating.

In some embodiments, the heating device includes a rigid pressing layer for pressing the sealing cover on the microplate. In some embodiments, the pressing layer is fixed to the supporting layer in opposite relationship with respect to the heating element. In some embodiments, the heating element includes an isolating layer made of thermally isolating material such as polytetrafluoroethylene (PTFE) sandwiched in-between the supporting and pressing layers so as to inhibit heat transfer from the supporting layer to the pressing layer. Accordingly, heat uptake of the pressing layer and heat loss can advantageously be further reduced so as to improve power efficiency in operating the instrument.

In some embodiments, the holder for holding the microplate is provided with one or more resilient elements such as compression springs or elastic gum counteracting the pressing force of the pressing layer in order to obtain a homogenous contact pressure and to level the microplate. Otherwise, a full contact of the sealing cover with close fit to the microplate even in case of a slightly non-planar microplate can advantageously be obtained. In some embodiments, the microplate is made of plastic material having a plate height of a few millimeters so that the microplate has sufficient flexibility to be planarized under action of the pressing layer. In some embodiments, the rigid pressing layer is additionally and/or alternatively being used for levelling the microplate.

According to a second aspect of the invention, a new system for processing, in particular thermally processing (e.g. incubating) and/or analyzing liquid samples such as reaction mixtures is proposed. The system of the invention can be configured in various ways in accordance with specific demands of the user. Stated more particularly, the system of the invention can be used for processing liquid samples wherein processing of the liquid samples involves pipetting of the samples by means of one or more pipettors. Accordingly, in some embodiments, the samples are subject to pipetting operations prior to heat-sealing the wells of the microplate, e.g., to pipette the samples into the wells and/or to add fluids to and/or to remove aliquots from the samples contained in the wells. In some embodiments, the samples contained in the wells are subject to pipetting operations after heat-sealing the wells, e.g., to add fluids to the samples contained in the wells and/or to remove aliquots therefrom. Additionally or alternatively, the system of the invention can be used for analyzing liquid samples contained in the heat-sealed wells by means of one or more analytical compartments for performing tests and assays related to various immunochemical and/or clinical-chemical analysis items.

In some embodiments, the system is adapted to thermally process reaction mixtures contained in the heat-sealed wells to be put through a series of temperature excursions, e.g., for performing the PCR or any other reaction of the nucleic acid amplification type. Specifically, transparent sealing covers enable quantitative real-time PCR by optically detecting the reaction products obtained during progress of the reactions. Reaction mixtures for thermal processing by the system of the invention typically include biological material containing nucleic acids but may also contain any other substance of interest as long as the processing thereof requires thermal treating. According to the invention, the system is equipped with at least one instrument for automatically heat-sealing a microplate as above-detailed.

According to a third aspect of the invention, a new method for automatically heat-sealing a microplate provided with a plurality of open-top wells for receiving liquid samples such as reaction mixtures for thermally cycling through a series of temperature excursions is proposed. The method of the invention comprises a step of disposing a thermally fixable sealing cover over the microplate. In some embodiments, the thermally fixable sealing cover is a thermally fusible sealing cover. In some embodiments, the thermally fixable sealing cover is provided with an adhesive material which can be thermally activated. The method comprises a further step of heating the sealing cover so as to fix the sealing cover to the microplate and a yet further step of actively cooling the microplate so that the temperature of the liquid reaction mixtures contained in the wells is kept below a predefined temperature when heating the sealing cover. In some embodiments, when heating the sealing cover, the temperature of the liquid reaction mixtures contained in the wells is kept below a predefined critical temperature lower than temperature excursions when performing the PCR. In some embodiments, the microplate is actively cooled simultaneously with heating the sealing cover. In some embodiments, the microplate is actively cooled prior to heating the sealing cover. In some embodiments, the microplate is actively cooled prior to and simultaneously with heating the sealing cover.

In some embodiments, the sealing cover is exclusively heated in regions in opposite relationship with respect to protruding rims surrounding openings of the wells. Accordingly, the sealing cover is not heated in regions other than those regions. In some embodiments, the sealing cover is exclusively heated in regions located in-between adjacent openings of the wells. Accordingly, the sealing cover can exclusively be heated in selected regions where adhesion to the microplate is to be reached only so as to reduce the total heat input to the microplate.

In some embodiments, the sealing cover is pressed on the microplate while the sealing cover is heated. In some embodiments, the pressing action ends after stopping heating the sealing cover. In some embodiments, it can be preferred that the pressing action ends after having the sealing cover solidified. Accordingly, in some embodiments involving the use of a thermally fusible sealing cover, the pressing action can continue until a solidified state of the sealing cover is reached advantageously enabling an easy and cost-efficient construction of the sealing cover.

In some embodiments, the microplate is cooled prior to starting heating the sealing cover so as to start heat-sealing of the microplate with a pre-cooled microplate containing pre-cooled reagent mixtures. In some embodiments, the microplate is cooled after heat-sealing so as to cool the reagent mixtures contained in the wells prior to thermal cycling. Accordingly, the sealing arrangement can advantageously be used as cool storage for storing the microplate before and/or after the heat sealing.

BRIEF DESCRIPTION OF THE FIGURES

Other and further objects, features and advantages of the invention will appear more fully from the following description. The accompanying drawings, together with the general description given above and the detailed description given below, serve to explain the principles of the invention.

DETAILED DESCRIPTION OF THE INVENTION

By way of illustration, specific exemplary embodiments in which the invention may be practiced now are described. In this regard, terminology with respect to orientations and directions such as "horizontal", "vertical", "upper", "lower" is used with reference to the orientation of the figure being described. Because components described can be positioned in a number of different orientations, this terminology is used for the purpose of illustration only and is in no way limiting.

Figure 1:
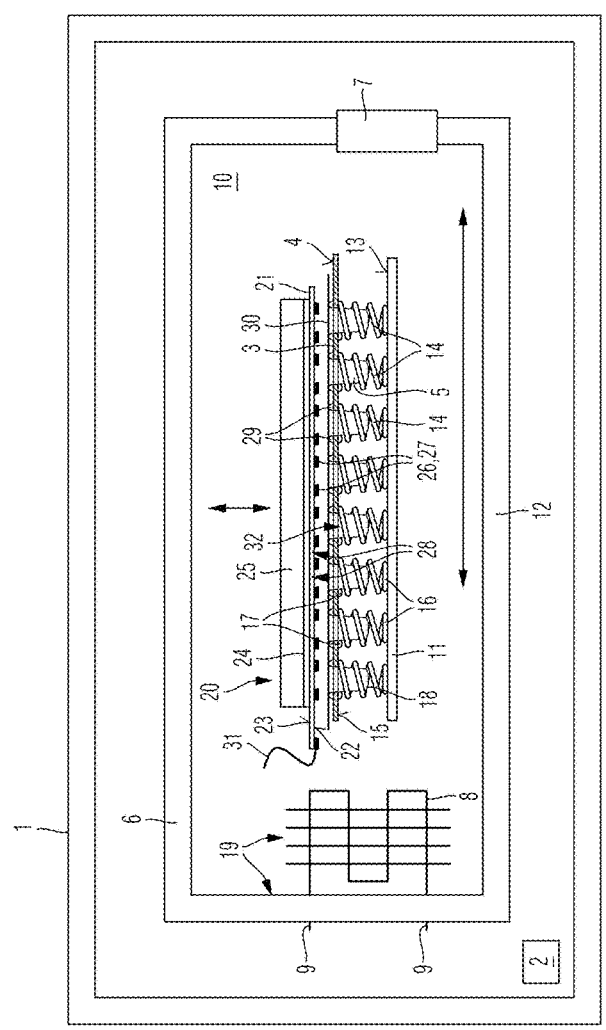
FIG. 1 shows a schematic sectional view of an exemplary instrument of the invention.

First, reference is made to FIG. 1. Accordingly, in some embodiments, an instrument generally referred to at reference numeral 1 for heat-sealing a microplate 3, includes a cooling device 19 comprising a closed instrument casing 6 forming an internal instrument space 10 which can be actively cooled. As detailed in the introductory portion, the term "closed" relates to a casing 6 which can be provided with openings or ports. With continued reference to FIG. 1, in some embodiments, the internal instrument space 10 can be cooled by means of a cooling coil 8. The cooling coil 8 penetrates the instrument casing 6. On its ends it is provided with fluid ports 9 for supplying cooling fluid such as water or air for circulating through the cooling coil 8. It is to be appreciated that any other technique for cooling the internal instrument space 10 can also be used. Specifically, in some embodiments, cooling of the internal space 10 can alternatively be based on thermoelectric devices using the Peltier effect.

With continued reference to FIG. 1, in some embodiments, the instrument 1 includes a tray 11 supporting the microplate 3 in horizontal position. In some embodiments, the tray 11 is slidably mounted to a base 12 enabling a repetitive, bidirectional movement between an operative or sealing position inside the instrument casing 6 for heat-sealing the microplate 3 and an inoperative or loading/unloading position outside the instrument casing 6 for loading/unloading the microplate 3 on/from the tray 11. As schematically illustrated in FIG. 1, in some embodiments, the instrument casing 6 is provided with a microplate port 7 so that the tray 11 can be horizontally moved through the microplate port 7. The microplate port 7 can be closed or opened by a closing means such as a door (not illustrated) so as to enable transport of the tray 11 with or without microplate 3 through the microplate port 7. Since such sliding mechanism is well-known to those of skill in the art, it need not be further elucidated herein. In some embodiments, the instrument 1 includes a moving mechanism for automatically moving the tray 11 between its sealing and loading/unloading positions. Since such moving mechanism is also well-known to those of skill in the art, it need not be further elucidated herein.

In some embodiments, an upper plate surface 4 of the microplate 3 forms a plurality of open-top wells 5 for receiving liquid samples such as reaction mixtures for performing the PCR which typically include biological material containing nucleic acids. With continued reference to FIG. 1, in some embodiments, the wells 5 are regularly arranged in a two-dimensional array of, e.g., ninety-six wells 5 comprised of eight columns and twelve rows intersecting each other at right angles. It, however, is to be appreciated that any other number of wells 5 may be envisaged according to the specific demands of the user. In some embodiments, the microplate 3 is an integrally moulded plastic disposable intended for single use only.

Further referring to FIG. 1, in some embodiments, the tray 11 is provided with a plurality of helical compression springs 14. As illustrated, in some embodiments, the compression springs 14 are arranged in correspondence to the wells 5 of the microplate 3 whereupon the number of compression springs 14 may, e.g., correspond to the number of the wells 5. Each of the compression springs 14 can, e.g., be adapted to accommodate one well 5 in a close fit. With continued reference to FIG. 1, in some embodiments, the compression springs 14 are in an upright position relative to an upper tray surface 13 in parallel alignment with respect to each other. Having their lower and upper ends 16, 17 in contact with the tray 11 and microplate 3, respectively, the helical compression springs 14 can elastically be compressed between the tray 11 and the microplate 3. Grace to a non-zero freeboard 18 between the wells 5 and the upper tray surface 13, the microplate 3 can vertically be moved against the elastic force of the compression springs 14. Otherwise, by effect of inserting the wells 5 into the compression springs 14, the microplate 3 is horizontally secured by the compression springs 14. In some embodiments, the instrument 1 is equipped with one or more resilient means other than compression springs 14 such as an elastic gum or rubber for elastically holding the microplate 3.

In some embodiments, the instrument 1 further includes a heating device 20 which, with continued reference to FIG. 1, in some embodiments, comprises a thin supporting layer 21, e.g., made of electrically isolating material having a low thermal capacity such as a ceramic or plastic material. The supporting layer 21 can, e.g., be made of polyimide having a layer thickness as small as 0.5 mm.

With continued reference to FIG. 1, in some embodiments, a heating element 26 adapted for generating Ohmic heat is fixed to a lower layer surface 22 of the supporting layer 21. In some embodiments, the heating element 26 includes a plurality of electrically conductive heating lines 27 connected to a connecting line 31 for supplying electric current to the heating element 26. In some embodiments, the heating lines 27 are embedded in a carrier layer (not illustrated) made of isolating material such as plastic enabling the heating element 26 to be readily fixed to the supporting layer 21.

As illustrated in FIG. 1, in some embodiments, an isolating layer 24 made of isolating material is fixed to an upper layer surface 23 of the supporting layer 21. The isolating layer 24 can, e.g., be made of polytetrafluoroethylene (PTFE) commonly known as Teflon and have a layer thickness in the range of from 3 to 5 mm. Those of skill in the art will appreciate that any other material and/or layer thickness can be envisaged according to the specific demands of the user.

With continued reference to FIG. 1, in some embodiments, a rigid pressing layer 25 is fixed to the upper side of the isolating layer 24. The pressing layer 25 can, e.g., be made of aluminium and have a layer thickness of 10 mm. However, other rigid materials and/or other layer thicknesses can be envisaged according to the specific demands of the user. Sandwiched in-between the supporting and pressing layers 21, 25, the isolating layer 24 inhibits heat transfer from the supporting layer 21 to the pressing layer 25.

As schematically illustrated in FIG. 1, in some embodiments, the heating device 20 can be vertically moved so as to bring the heating element 26 in and out of physical contact with a thermally fusible sealing cover 30 located over the microplate 3 adjacent the wells 5. In some embodiments, the sealing cover 30 is placed on the upper plate surface 4 of the microplate 3. Since such moving mechanism is well-known to those of skill in the art, it need not be further elucidated herein. Due to the rigid pressing layer 25 backing the supporting layer 21, the sealing cover 30 can be pressed on the microplate 3 while heated by the heating element 26 acting against the elastic forces of the helical compression springs 14. Due to the resilient forces of the helical compression springs 14, a homogeneous pressure force can act on the microplate 3 for levelling the microplate 3 at a pre-defined height. Otherwise, under action of the heating device 20, the microplate 3 can be pressed downwards using the freeboard 18 to thereby ensure a close fit of the sealing cover 30 even in case of a slightly non-even microplate 3 which can be planarized.

With continued reference to FIG. 1, in some embodiments, the heating lines 27 form a mesh-like wired structure adapted to contact the sealing cover 30 exclusively in regions where the sealing cover 30 is in opposite relationship to rims 29 projecting from the upper plate surface 4. Each of rims 29 surrounds an opening 32 of one well 5. Accordingly, the sealing cover 30 can exclusively be heated, e.g., fused at the rims 29. Otherwise, as illustrated in FIG. 1, non-heated zones 28 between the heating lines 27 are in opposite relationship with respect to the openings 32 of the wells 5 when the heating element 26 contacts the sealing cover 30 for heat-sealing.

In some embodiments, as illustrated in FIG. 1, the instrument 1 further includes an instrument controller 2 set up to control heat-sealing of the microplate 3. The instrument controller 2 can, e.g., be embodied as programmable logic controller running a computer-readable program. The instrument controller 2 is electrically connected to the instrument components which require control and/or provide information which include the cooling device 19 and the heating device 20.

In practical use, under control of the instrument controller 2, in some embodiments, the tray 11 is horizontally moved through the microplate port 7 into inoperative position outside the instrument casing 6 where the microplate 3 containing the liquid samples such as reaction mixtures can be put on the tray 11. The tray 11, together with the microplate 3, is then horizontally moved into operative position inside the instrument casing 6 where the microplate 3 is kept ready for heat-sealing.

In some embodiments, the thermally fixable sealing cover 30 is placed over the microplate 3 in sealing position. In some other embodiments, the sealing cover 30 is placed over the microplate 3 prior to transporting the microplate 3 into sealing position, particularly in a situation where the microplate 3 is located outside the instrument casing 6.

In some embodiments, the heating device 20 is vertically moved until the heating element 26 is in thermal communication with the sealing cover 30 so as to heat, e.g., thermally fuse the sealing cover 30 in regions opposing the rims 29. With reference to FIG. 1, is can be preferred that the heating device 20 is vertically moved until the heating element 26 is in (physical) contact with the sealing cover 30. In some embodiments, the heating device 20 is pressed on the microplate 3 simultaneously with heating the sealing cover 30.

In some embodiments, the microplate 3 is actively cooled prior and simultaneously with heating the sealing cover 30 so as to prevent the liquid samples from experiencing an undesired high temperature increase so that, e.g., in the case of performing the PCR, the temperature of the reaction mixtures is below a pre-defined critical temperature. In some embodiments, the predefined temperature can be 40° C. which can sometimes be considered critical for initiating unspecific nucleic acid amplification. In some embodiments, e.g., starting with reaction mixtures having a temperature of about 32° C., a temperature increase of the reaction mixtures contained in the wells 5 is below 5° C.

Heating of the sealing cover 30 then is stopped, e.g., to have the sealing cover 30 solidified so as to cause adherence of the sealing cover 30 to the microplate 3 in order to air-tightly seal the wells 5. In some embodiments, the pressing action of the heating device 20 is stopped not before the sealing cover 30 is in a fully solidified state.

In some embodiments the sealing zone is actively cooled to accelerate solidification of the sealing cover 30 (sealing foil) and/or molten portions of the microplate 3. Such active cooling can e.g. be done by a fan (not illustrated). Those of skill in the art will appreciate that any other means for actively cooling the sealing cover 30 accommodated in the instrument space 10 of the instrument 1 can be envisaged according to the specific demands of the user. Specifically, the heating device 20 can for instance include a plurality of thermoelectric devices (Peltier devices) which based on the Peltier effect and depending on the direction of the current applied can be operated to alternatively heat or cool the sealing cover 30.

The heating device 20 is then moved upwards, followed by moving the tray 11 into the inoperative position outside the instrument casing 6 so that the microplate 3 can be removed from the tray 11 for further processing, i.e. thermal cycling, of the reaction mixtures contained therein.

Accordingly, in the case of performing the PCR, unspecific amplification of reaction mixtures contained in the wells 5 caused by heat-sealing the microplate 3 can advantageously be avoided. Due to the combined measures that
  the sealing cover 30 is exclusively heated in regions opposing the rims 29,
  the sealing cover 30 is not heated in regions opposing the openings 32 of the wells 5,
  the supporting layer 21 (and also the heating element 26) has a low thermal capacity, and heat transfer to the pressing layer 25 is strongly inhibited by the isolating layer 24, various synergistic positive effects, e.g., with respect to a low heat input into the instrument casing 6 for heat-sealing the microplate 3 and low heat loss inside the instrument casing 6 during and following the heat-sealing process in the cooling-off period of the heating device 20 and thereby an improved power efficiency can be obtained. Otherwise, the heating element 26 can quickly be heated and cooled to thereby reduce the time interval needed for heat-sealing the microplate 3. In the case of using a thermally fusible sealing cover 30, due to the quick cooling, another major advantage is given by the fact that pressing of the sealing cover 30 to the microplate 3 can also be stopped after having the sealing cover 30 fully solidified thus enabling a simple and cost-effective structure of the sealing cover 30. Stated more particularly, in contrast to the conventional construction, the sealing cover 30 may not necessarily have a laminated structure consisting of several individual layers such as a fusible layer, adhesive layer and separating layer so as to not cause a poorly adhering or even damaged sealing cover when removing the heating element 26. Accordingly, the sealing cover 30 can be produced in a highly cost-effective manner. Otherwise, optical transparency of the sealing cover 30 can be improved. Solidification of the sealing cover 30 can also be accelerated by actively cooling the sealing cover 30.

According to the invention, it is highly preferred to provide for a closed instrument casing 6 in line with understanding of the term "closed" as detailed in the introductory portion the internal instrument space 10 of which can be actively cooled, inter alia, for the following reasons:

formation of condensate on the microplate 3 is largely reduced, in case of using a thermally fusible sealing cover 30, there is a quicker solidification of the fused sealing cover 30, the tray 11 can already be in a pre-cooled condition prior to starting heat-sealing the microplate 3 saving time to heat-seal the microplate 3.

In some alternative embodiments, not illustrated in FIG. 1, integrated heating and cooling devices 19, 20 can be used, e.g., configured as one or more thermoelectric devices such as Peltier devices. Depending on the direction of current applied, the thermoelectric devices can alternatively produce or absorb heat.

Figure 2:
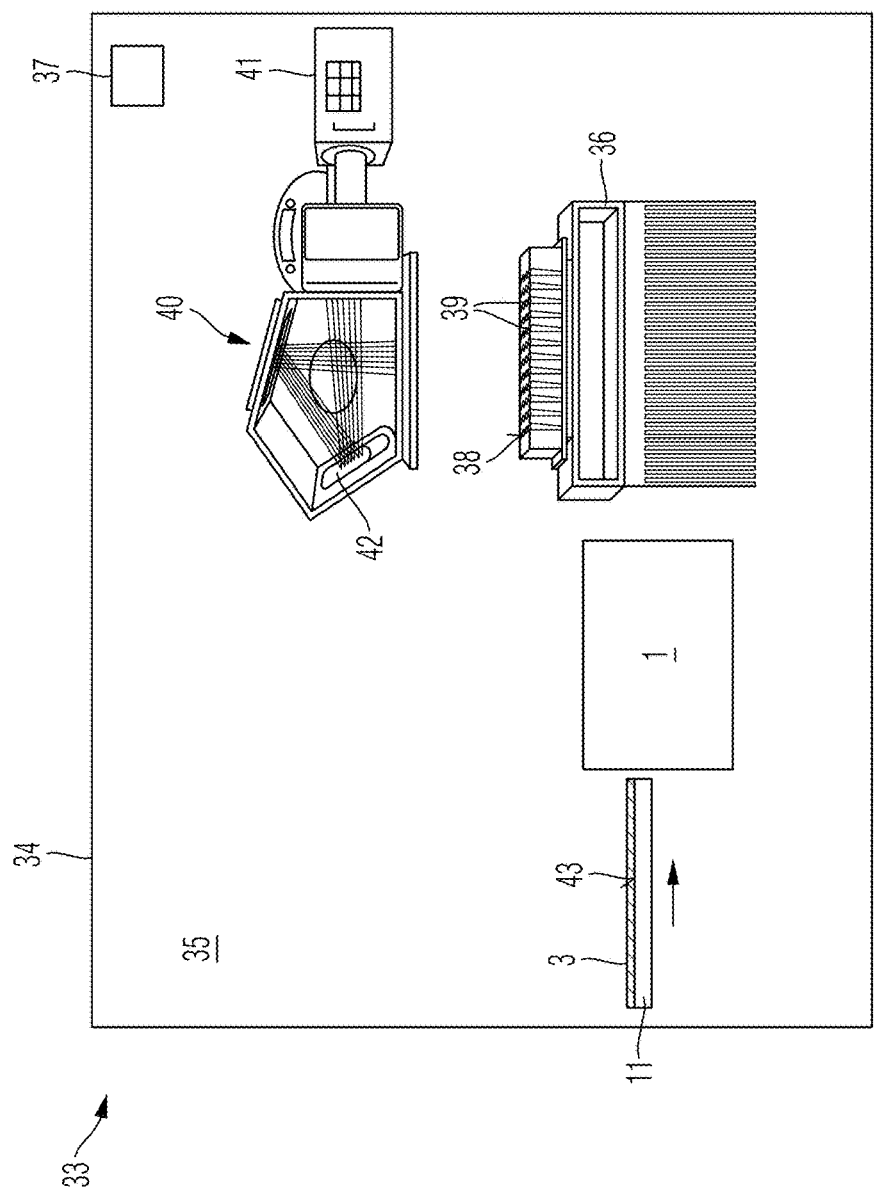
FIG. 2 shows a schematic perspective view of an exemplary system of the invention.

Reference is now made to FIG. 2 illustrating a schematic diagram of an automated system for thermally processing liquid samples. In some embodiments, the system is used for cycling liquid reaction mixtures through a series of temperature excursions for performing the PCR or any other reaction of the nucleic acid amplification type.

As illustrated in FIG. 2, in some embodiments, the system generally referred to at reference numeral 33 includes a closed system casing 34 (in line with the understanding of the term "closed" as detailed in the introductory portion) forming an internal system space 35, inter alia, containing the instrument 1 for heat-sealing microplates 3 as illustrated in FIG. 1. In some embodiments, the tray 11 is adapted for supporting the microplate 3 in horizontal position on an upper tray face 43. The tray 11 enables a repetitive, bidirectional movement between the internal system space 35 for loading or unloading the microplate 3 on/from the tray 11 and the internal instrument space 10 of the instrument 1 for heat-sealing the microplate 3 prior to thermally processing the reaction mixtures contained in the wells 5. Since such sliding mechanism is well-known to those of skill in the art, it need not be further elucidated herein.

With continued reference to FIG. 2, in some embodiments, the internal system space 35 accommodates a temperature-controlled block 36 for heating and/or cooling the liquid reaction mixtures. In some embodiments, the temperature-controlled block 36 contains thermoelectric devices (not further detailed) using the Peltier effect. On its upper surface the temperature-controlled block 36 has a generally planar seat 38 for accommodating the microplate 3. The seat 38 is provided with a plurality of recesses 39 for receiving the wells 5 of the microplate 3 in close fit with at least partially full contact for thermal communication between the wells 5 and the temperature-controlled block 36.

Accordingly, the reaction mixtures contained in the wells 5 of the microplate 3 can be thermally cycled through a series of temperature excursions. Specifically, in the PCR, a multiply repeated sequence of steps for the amplification of nucleic acids is done, wherein in each sequence the nucleic acids are melted (denaturated) to obtain denatured polynucleotide strands, primers are annealed to the denatured polynucleotide strands, and the primers are extended to synthesize new polynucleotide strands along the denaturated strands to thereby obtain new copies of double-stranded nucleic acids.

With continued reference to FIG. 2, in some embodiments, the system 33 includes a detection arrangement generally referred to at reference numeral 40 for optically detecting the reaction products of the amplification steps. Stated more particularly, the detection arrangement 40 is positioned to detect emission beams emitted from the wells 5 of the microplate 3 placed on the seat 38. With yet continued reference to FIG. 2, in some embodiments, the detection arrangement 40 includes one or more detectors 41 for optically detecting the emitted light such as, but not limited to, charge coupled devices (CCDs), diode arrays, photomultiplier tube arrays, charge injection devices (CIDs), CMOS detectors and avalanche photo diodes. In some embodiments, the detection arrangement 40 also includes one or more excitation light sources such as lamps to excite emission of the emission beams from the reaction products. With yet continued reference to FIG. 2, in some embodiments, the detection arrangement 40 further includes light guiding elements 42 such as, but not limited to, lenses and mirrors and/or light separating elements such as, but not limited to, transmission gratings, reflective gratings and prisms. Specifically, radiation such as excitation light can be transmitted to the reaction mixtures and (e.g. fluorescent) light emitted to the one or more detectors 41 can be detected. Specifically, in the detection arrangement 40, the reaction products can also be detected during the progress of the reactions commonly known as real-time PCR. Since the optical detection of reaction products is well-known to those of skill in the art, it is not further elucidated herein.

The system 33 further includes a system controller 37 set up to control thermal processing of the reaction mixtures. In some embodiments, the system controller 37 can also be set-up for automatically heat-sealing the microplate 3 and, thus, can be used instead of the instrument controller 2. The system controller 37 can, e.g., be embodied as programmable logic controller running a computer-readable program. The system controller 37 is electrically connected to the system components which require control and/or provide information which include the temperature-controlled block 36, the detection arrangement 40 and, optionally, the instrument 1.

In practical use, under control of the system controller 37, in some embodiments, the tray 11 loaded with the microplate 3 provided with the reaction mixtures is horizontally moved into the instrument 1 for thermally fixing the sealing cover 30 to the microplate 3. The microplate 3 is then placed on the temperature-controlled block 36 for thermal processing of the reaction mixtures, e.g., using the tray 11. Otherwise, in some embodiments, the tray 11 is used for moving the microplate 3 into and/or out of the internal system space 35.

Figure 3:
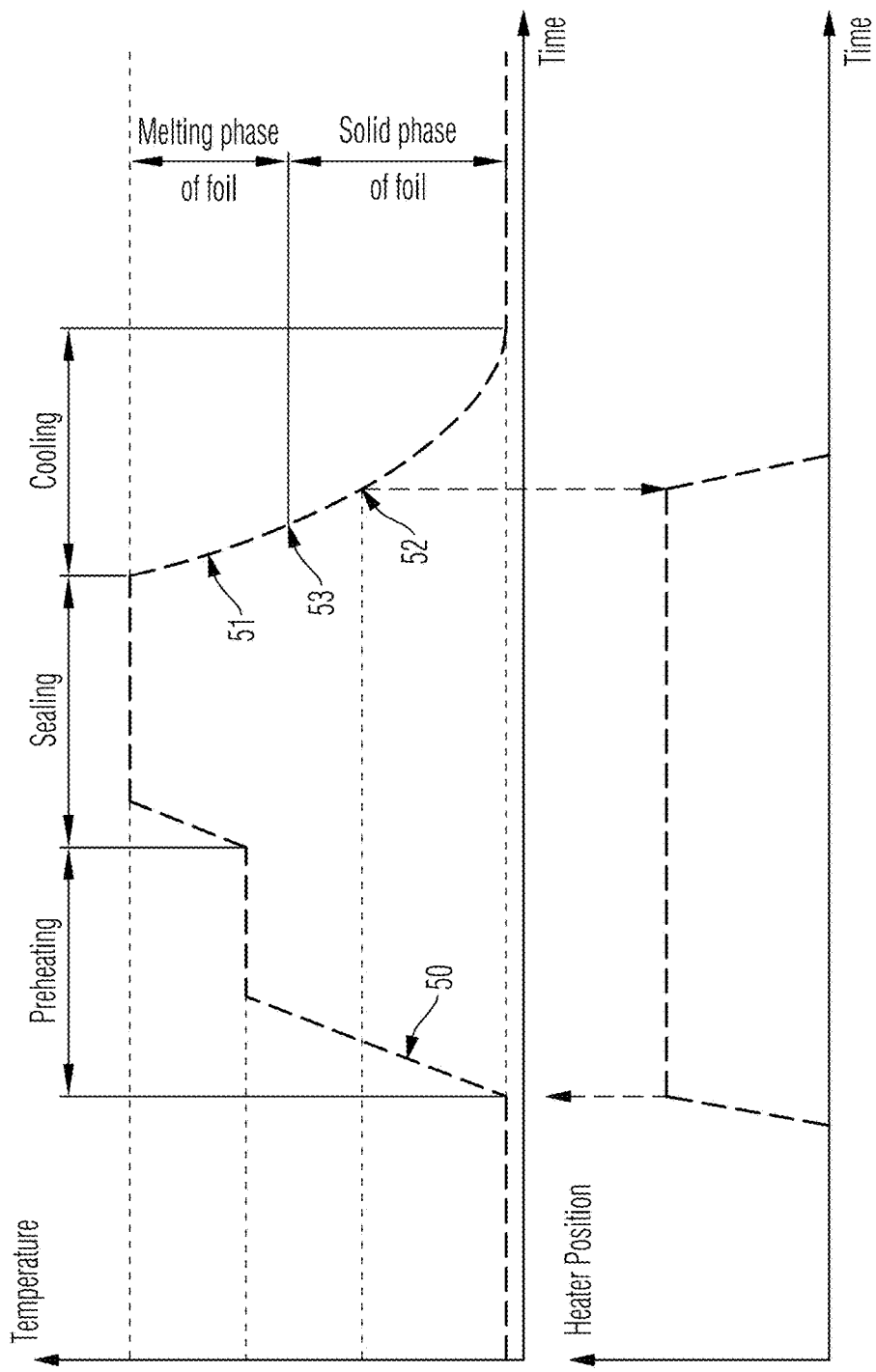
FIG. 3 shows a process scheme of sealing a sealing cover to a microplate

FIG. 3 shows an exemplary process scheme for sealing the thermally fixable sealing cover 30 onto the microplate 3. The upper section of FIG. 3 depicts the temperature of the heated portions of the heating device 20 ("heater") over time and the lower section thereof illustrates the vertical position of the heater relative to the sealing cover 30 over time. Generally, the sealing process can be divided into several consecutive phases, i.e., a preheating phase, a sealing phase and a cooling phase.

With continued reference to FIG. 3, prior to the preheating phase, the heater is moved towards the sealing cover 30 and placed thereon so as to generate mechanical pressure acting on the sealing cover 30 to press the sealing cover 30 onto the microplate 3. Specifically, in the curve depicted in the lower section of FIG. 3, the ramp increasing over time indicates the movement of the heater towards the sealing cover 30 to build up mechanical pressure acting on the sealing cover 30, the constant portion thereof indicates a non-varied position of the heater so as to keep a constant mechanical pressure acting on the sealing cover 30, and the ramp decreasing over time indicates the movement of the heater away from the sealing cover 30 to release the mechanical pressure acting on the sealing cover.

During the preheating phase the temperature of the heated portions of the heating device 20 is ramped up, as indicated by ramp up phase 50, to a temperature above the melting point of the employed sealing cover 30. During the preheating phase, the heater position is not varied so as to keep the mechanical pressure of the heater acting against the sealing cover 30 constant.

During the sealing phase the temperature of the heating device 20 is further raised to a predetermined level and then is kept constant. During the sealing phase, the heater position is not varied to further keep the mechanical pressure of the heater against the sealing cover 30 constant to melt the sealing cover 30 and the microplate 3 together.

The cooling phase is divided in two periods, i.e., a first cooling period 51 and a second cooling period 52. During the first cooling period 51 the heater position is not varied so as to still keep the mechanical pressure acting on the sealing cover 30 constant until the temperature of the sealing cover 30 falls below the melting temperature 53 of the sealing cover 30. Only then, in the second cooling period 52, the heater is moved away from the sealing cover 30 to release the mechanical pressure acting on the sealing cover 30. In the cooling phase, the sealing cover 30 can be passively or actively cooled.

With such a sealing process simple one layer sealing cover foils may be employed. Such foils are on the one hand cheaper and on the other hand have better optical properties than sealing covers where two or more foils are laminated together.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

REFERENCE LIST

1 Instrument
2 Instrument controller
3 Microplate
4 Upper plate surface
5 Well
6 Instrument casing
7 Microplate Port
8 Cooling coil
9 Fluid port
10 Instrument space
11 Tray
12 Base
13 Upper tray surface
14 Compression spring
15 Lower plate surface
16 Lower end
17 Upper end
18 Freeboard
19 Cooling device
20 Heating device
21 Supporting layer
22 Lower layer surface
23 Upper layer surface
24 Isolating layer
25 Pressing layer
26 Heating element
27 Heating line
28 Non-heated zone
29 Rim
30 Sealing cover
31 Connecting line
32 Opening
33 System
34 System casing
35 System space
36 Block
37 System controller
38 Seat
39 Recess
40 Detection arrangement
41 Detector
42 Light guiding element
43 Upper tray face
50 Ramp up phase
51 First cooling period
52 Second cooling period
53 Melting temperature

What is claimed:

1. A method for automatically heat-sealing a microplate provided with a plurality of open-top wells surrounded by protruding rims, said wells being configured for receiving liquid samples, said method comprising the following steps:
 disposing a thermally fixable sealing cover over said microplate, wherein said sealing cover comprises regions in opposite relationship with respect to said protruding rims;
 contacting said regions of said sealing cover with a heating device comprising (a) a plurality of discrete electrically conductive heating elements each individually configured to generate Ohmic heat, and (b) a plurality of non-heated zones positioned adjacent to the heating elements and in opposite relationship with respect to the open-top wells;

exclusively heating the plurality of discrete electrically conductive heating elements and thermally fixing the regions of said sealing cover to said microplate; and actively cooling said microplate in a manner that a temperature of said liquid samples is kept below a predefined temperature when heating said sealing cover.

2. The method according to claim 1, in which said sealing cover is pressed on the microplate while heating said sealing cover, wherein said pressing is not stopped before solidification of the sealing cover is reached.

3. The method according to claim 1, wherein said microplate is cooled prior to starting heating said sealing cover and/or after heat-sealing said microplate.

4. The method according to claim 1, wherein the heating step comprises:

preheating the heating elements by ramping up the temperature of the heating elements to a temperature above the melting point of the sealing cover;

maintaining the temperature above the melting point of the sealing cover at a constant level for a period of time during the preheating step; and sealing the sealing cover and the microplate together by raising the temperature of the heating elements further to a predetermined level.

5. A method for automatically heat-sealing a microplate provided with a plurality of open-top wells for receiving liquid samples, wherein said microplate comprises protruding rims surrounding openings of said wells, said method comprising the following steps:

disposing a thermally fixable sealing cover over said microplate, wherein said sealing cover comprises regions in opposite relationship with respect to said protruding rims;

contacting said regions of the sealing cover with a heating device comprising (a) a plurality of discrete electrically conductive heating elements each individually configured to generate Ohmic heat, and (b) a plurality of non-heated zones positioned adjacent to the heating elements and in opposite relationship with respect to the open-top wells, and generating a mechanical pressure acting on the sealing cover to press the sealing cover onto the microplate;

exclusively heating the plurality of discrete electrically conductive heating elements and thermally fixing the regions of the sealing cover to said microplate, the heating and fixing step comprises (i) preheating the heating elements by ramping up the temperature of the heated elements to a temperature above the melting point of the sealing cover while maintaining the mechanical pressure acting on the sealing cover; (ii) maintaining the temperature above the melting point of the sealing cover at a constant level for a period of time during the preheating step; and (iii) sealing the sealing cover and the microplate together by raising the temperature of the heating elements further to a predetermined level and kept constant while maintaining the mechanical pressure acting on the sealing cover;

cooling the heating elements to a temperature below the melting temperature of the sealing device while maintaining the mechanical pressure acting on the sealing cover; and moving the heating device away from the sealing cover and releasing the mechanical pressure acting on the sealing cover.

6. The method according to claim 5, further comprising actively cooling said microplate in a manner that a temperature of said liquid samples is kept below a predefined temperature when heating said sealing cover.

* * * * *